United States Patent [19]

Munakata et al.

[11] Patent Number: 4,827,143
[45] Date of Patent: May 2, 1989

[54] MONITOR FOR PARTICLES OF VARIOUS MATERIALS

[75] Inventors: Chusuke Munakata, Tokyo; Yoshitoshi Itoh, Ome, both of Japan

[73] Assignee: Hitachi, Ltd., Tokyo, Japan

[21] Appl. No.: 30,436

[22] Filed: Mar. 26, 1987

[30] Foreign Application Priority Data

Mar. 26, 1986 [JP] Japan ............................ 61-65646
Jun. 4, 1986 [JP] Japan ............................ 61-127909

[51] Int. Cl.$^4$ .......................................... G01N 15/06
[52] U.S. Cl. ................................. 250/574; 250/227; 356/339
[58] Field of Search ............... 250/227, 574, 222.2, 250/573, 575; 356/337–340, 342; 350/96.1

[56] References Cited

U.S. PATENT DOCUMENTS

| 4,146,799 | 3/1979 | Pitt et al. ........................ 250/574 |
| 4,267,509 | 5/1981 | Graham ........................... 356/338 |
| 4,420,256 | 12/1983 | Fladda et al. .................... 250/574 |
| 4,678,326 | 7/1987 | Harjunmaa ....................... 250/574 |
| 4,696,571 | 9/1987 | Goldberg et al. ................. 250/574 |
| 4,707,134 | 11/1987 | McLachlan et al. ............... 250/574 |

FOREIGN PATENT DOCUMENTS

| 0011290 | 2/1975 | Japan . |
| 0136475 | 11/1976 | Japan . |
| 0019653 | 2/1982 | Japan . |
| 0053738 | 3/1983 | Japan . |

OTHER PUBLICATIONS

Van Nostrand's Scientific Encyclopedia, Fifth Edition, edited by Douglas Considine, Van Nostrand Reinhold Co. 1976, p. 1606.

Primary Examiner—David C. Nelms
Attorney, Agent, or Firm—Antonelli, Terry & Wands

[57] ABSTRACT

A monitor for particles of various materials which counts the number of the particles on real-time and in situ basis. The monitor comprises a unit for illuminating an object to be inspected with an illumination light beam of a predetermined cross-sectional area, a unit for detecting a change in optical mode of the illumination light beam caused by the particles being contained in the inspected object and illuminated with the illumination light beam, the illuminating and detecting units being of a unitary structure, and a unit for counting an amount of the particles contained in the inspected object by using a change in intensity of an optically mode changed light beam.

6 Claims, 6 Drawing Sheets

MONITOR FOR PARTICLES OF VARIOUS MATERIALS

BACKGROUND OF THE INVENTION

This invention relates to a monitor for particles of various materials which counts, on in-line and real-time basis, particles of various materials present in a variety of liquids which are used in a wet process in the course of a fabrication process of semiconductor devices.

As is well known, particles of various materials (various kinds of substances usually called dusts) cause contamination or the like of semiconductor, for example, irrespective of the fact that they are contained either in the liquids for the semiconductor fabrication process or in water or liquid chemicals for general use. Accordingly, many different makers have hitherto been engaged in developing and commercializing methods and apparatus for inspecting and counting particles of various materials present in liquids.

Many apparatus for inspection of particles have been available in the past and they are based on a variety of fundamental principles depending on utilization purposes. To sum up the principles on which the conventional apparatus of this type are based, there are three major categories of (1) an optical method, (2) an electrical method and (3) an ultrasonic method.

The ultrasonic method applies, as disclosed in for example JP-A-57-19653, techniques of a so-called sonar and inspection of a crack using an ultrasonic wave to the counting of particles in liquid but it suffers from poor reflection of the ultrasonic wave, especially, where the particles are biological cells and can not always be suitable for general purposes.

The electrical method detects, as disclosed in for example JP-A-58-53738, an increase in electrical resistance of a liquid due to replacement of part of the liquid in a pinhole with particles which pass through the pinhole. Originally, this method has been developed for counting red blood corpuscles in blood. Since the red blood corpuscles have each the size which is substantially constant, the pinhole will not be clogged if its size is larger than that of the red blood corpuscle. However, particles in the liquids used for the semiconductor fabrication process are different in size case by case with the result that the pinhole through which the particles to be counted pass may sometimes be clogged with the particles. This accounts for the fact that the electrical method is inconvenient for ordinary use in the semiconductor fabrication process involved with different sizes of particles and is not always suitable for general purposes as in the case of the ultrasonic method.

In conclusion, it is the first method, i.e., the optical method that has general compatibility with inspection for particles of various materials and can conveniently or safely be used for counting particles of unknown size. The optical method can be particularized by some family processes, of which two are closely related to the present invention and will be described below.

The noticeable first process originating from the optical method is for detecting scattering light from a particle, as will be taught from the disclosure of, for example, JP-A-51-136475.

An apparatus utilizing the scattering light is constructed in principle as shown in FIG. 6.

Referring to FIG. 6, a liquid 2 to be inspected is poured, together with particles 1, 1' (represented by black circular dots in the figure), into a special vessel 3. The liquid 2 is pressurized by a suitable device (not shown) to run past a nozzle 3a, turning into a jet 2'. The jet 2' enters a receptacle 4 and is usually discharged therefrom for disposal. For example, the jet 2' has a diameter of several of hundreds of microns and when the number of particles present in the liquid is relatively small (for example, as in the case of clean water most frequently used for the semiconductor fabrication process), the particles 1, 1' are aligned in the line and run off in jet together with the liquid 2, as best seen in FIG. 6. Accordingly, when the jet 2' is illuminated with a light beam 5 orthogonal to the jet 2', the light beam 5 illuminates the particles 1 one by one. For formation of the light beam 5, beams of light 5' from a light source such as a laser are converged by means of a lens 6.

When the particle 1 is illuminated with the light beam 5, two different phenomena take place as illustrated in FIG. 6. In the first phenomenon, photons constituting the light beam 5 are scattered at the surface of the particle 1, radiating a so-called beam of scattering light 7 in a direction different from the travelling direction of the light beam 5. The second phenomenon is that the light beam 5 is prevented from travelling, that is, stopped by the particle 1 and is not allowed to transmit to the right-hand side of the jet 2'.

The aforementioned scattering light beam 7 can persist in the presence of the particle 1 and therefore collapses as the particle 1 runs off toward the receptacle 4. Accordingly, passage of the particle 1 can be inspected by detecting the scattering light beam 7 by means of a photodetector 8.

Intensity of the scattering light from the particle 1 obtained in the manner described above is converted into an electrical signal as exemplified in FIG. 7A. In the example of FIG. 7A, three particles 1 are detected. Once the intensity of the scattering light is converted into electrical pulses, the number of pulses can be counted using a well known technique of electrical signal processing to count the number of particles 1 present in the liquid. By using the known volume of the liquid 2, the number of particles per unit volume can eventually be known quantitatively.

The second process originating from the optical method is called a light extinction process wherein transparent light is detected. The principle of this second process will be described by making reference to FIG. 6 again.

On the assumption that no particle 1 is present in the jet 2', the absence of an obstacle allows the incident light beam 5 to transmit through the jet 2', thus forming a transparent light beam 5'' which is detected by means of a photodetector 9. Intensity of the transparent light beam 5'' detected by the photodetector 9 is decreased with the existence of the particle 1, indicating that the transparent light beam 5'' extinguishes. Thus, as shown in FIG. 7B, the output waveform from the photodetector 9 changes decreasingly in one-to-one correspondence to the occurrence of the scattering light beam. As an example, the incident light beam 5 interferes with three particles in FIG. 7B. Obviously, the transparent light signal is equivalent to the scattering light signal shown in FIG. 7A and as is clear from the foregoing description, the number of particles in the liquid 2 can also be determined from the transparent light signal.

FIG. 8A illustrates another prior art example for counting particles by utilizing transmission light, which is applied, as disclosed in JP-A-50-11290, to a vessel for sedimentation adapted to remove particles from water mixed with particles. The optical method explained with reference to FIG. 6 is for counting on the so-called off-line basis wherein a small amount of liquid to be counted is averted from a real process so as to undergo sampling inspection and inevitably, it disadvantageously fails to perform real-time counting. Contrary to this, the process shown in FIG. 8A permits real-time counting.

Referring to FIG. 8A, a vessel for sedimentation 10 contains a liquid 2 in which particles 1, 1' are present. As the time elapses, the particle 1' initially present in an upper portion of the vessel 10 drops for sedimentation toward the bottom of the vessel 10.

Since the vessel 10 is typically made of an opaque material such as plastics or metal, an external light beam can not be admitted to the interior of the vessel 10. Accordingly, the side walls of the vessel 10 are partly bored and holes in the side walls are packed with a transparent material such as acrylic resin to form windows 11 and 11'. With this construction, a light beam 5 can transfer through the liquid 2 in the vessel 10. If the light beam 5 interferes with the particle 1, intensity of a transparent light beam 5'' decreases so that a photodetector 9 can produce an output signal which changes decreasingly in accordance with the presence of the particle as illustrated in FIG. 8B and the number of particles can be counted based on the principle set forth so far. Light 5' from a light source (not shown) is transmitted to the neighborhood of the vessel 10 through an optical fiber 12 and converted by a lens 6 into the parallel light beam 5.

The prior art methods and apparatus for counting particles in liquid, though filling the pertinent roles in the industrial fields, have some disadvantages when intended to be applied to the semiconductor fabrication process.

The first disadvantage results from the fact that the prior art system fails to perform the real-time counting in applications to the semiconductor fabrication process. Taking the scattering light process or the light extinction process explained with reference to FIG. 6, for instance, a small amount of liquid 2 is sampled and pured into the vessel of the counting apparatus in order for the particles in the liquid to be counted. During the counting, the number of particles present in the liquid being in use for the fabrication process changes with time and at the phase of completion of particle counting, the number of particles present in the liquid is different from that of the particles sampled and counted. The light extinction process shown in FIG. 8A permits the real-time counting but it is exclusively and effectively applicable to the sedimentation phenomenon, and can not be used for the semiconductor fabrication process involved with stirred liquid because the same particle is counted many times. In any case, the prior art system sequentially discriminates the particles 1 one by one to produce a corresponding electrical pulse and in principle, it is obviously unsuited for the real-time counting.

In the second place, the prior art system disadvantageously fails to perform "in situ" counting and this defect is closely related to the first disadvantage. For example, in FIG. 8A, the concentration of the particles is greater in the neighborhood of the bottom of the vessel 10 than in the neighborhood of the upper portion of the vessel 10. Eventually, the particles 1 hardly stay in the neighborhood of the upper portion of the vessel 10 and the upper part of the liquid 2 in the vessel becomes relatively clean. Therefore, with the aim of counting particles 1 near the bottom of the vessel 10, another transmission light detector resembling the detector shown in FIG. 8A must be additionally provided near the bottom of the vessel 10. This requires that the vessel for sedimentation 10 be additionally machined, resulting in considerable industrial unprofitableness. It follows therefore that as far as the prior art system is concerned, any "in situ" counting of desired portions of the vessel is practically impossible. When making an attempt to inspect the liquid sampled at desired portions by using the processes shown in FIG. 6, many samples of liquid must be prepared in relation to lapse of time because the state of the liquid mixed with particles under sedimentation changes with time and inspection results can be obtained only through time-consuming labors, proving that such an attempt is impractical.

SUMMARY OF THE INVENTION

An object of this invention is to provide a monitor for particles of various materials which can eliminate the two disadvantages of the prior art system described previously and which can afford to perform real-time and "in situ" counting.

According to the invention, the above object can be accomplished by a monitor for particles of various materials which comprises a unit for illuminating an object to be inspected with an illumination light beam of a predetermined cross-sectional area, a unit for detecting a change in optical mode of the illumination light beam caused by the particles being contained in the inspected object and illuminated with the illumination light beam, the illuminating and detecting units being of a unitary structure, and a unit for counting an amount of the particles contained in the inspected object by using a change in intensity of an optically mode changed light beam.

The monitor configured as above can afford to perform the real-time and "in situ" counting.

DESCRIPTION OF THE PREFERRED EMBODIMENTS

Prior to describing preferred embodiments of the present invention, the principle thereof will first be explained.

In order to achieve the real-time counting, which is the first difficulty encountered in the prior art system, a new counting method has to be adopted in place of counting the number of individual particles employed in the prior art system. To this end, according to the present invention, a great number of particles are counted simultaneously. More particularly, optical signals representative of beams of scattering light from a number of particles contained in a specified volume are optically added together and a resulting sum signal is detected by means of a single photodetector.

In order to achieve the "in situ" counting, which is the second difficulty faced by the prior art system, a number of particles are illuminated with light simultaneously and beams of scattering light from the particles are collected by means of optical members which are configured in a unitary and compact form and placed in the liquid being inspected. To this end, according to the present invention, optical fibers are exemplarily used as the optical members. Specifically, a bundle of optical fibers consisting of a plurality of optical fiber strands are used for either purpose of admitting the illumination light to the liquid being inspected and capturing the beams of scattering light from particles in the liquid.

Figure 5:
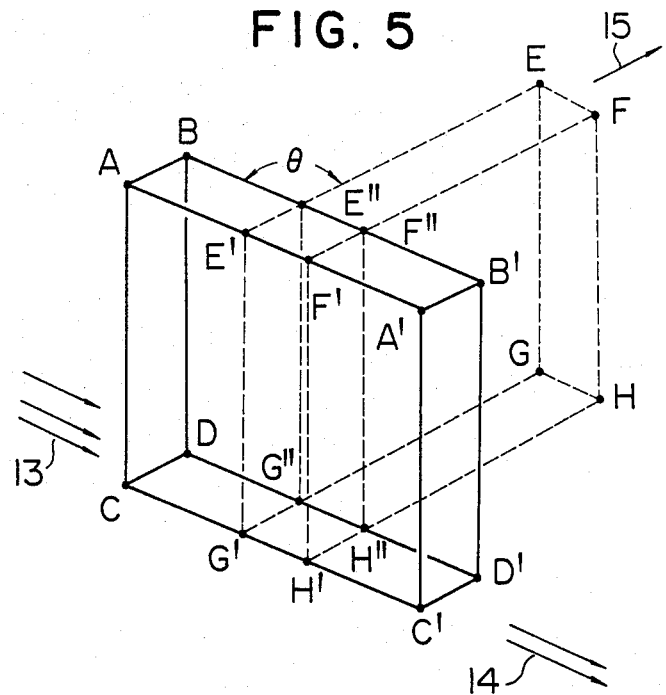
FIG. 5 is useful to diagrammatically explain the principle of the monitor of the present invention.
Figure 6:
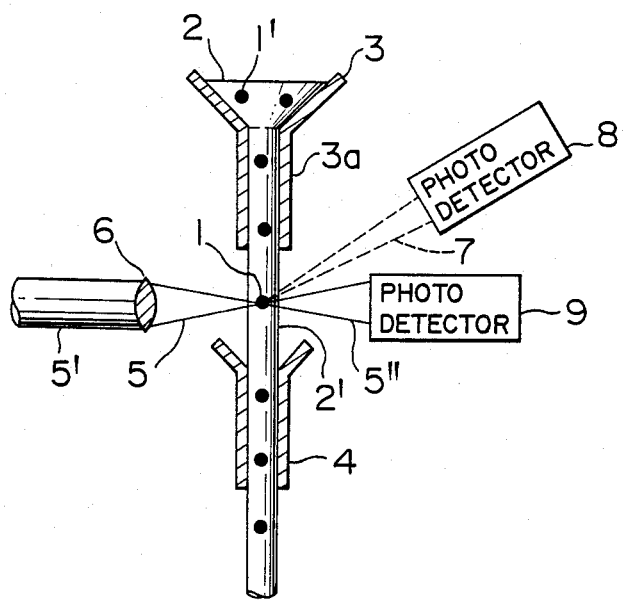
FIG. 6 diagrammatically shows the principle of a prior art inspection method.
Figure 7A:
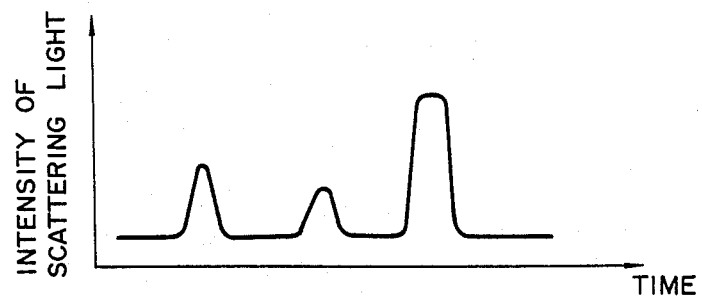
FIG. 7A is a graph illustrating dependence on time of intensity of scattering light caused by a passing particle pursuant to the prior art method of FIG. 6.
Figure 7B:
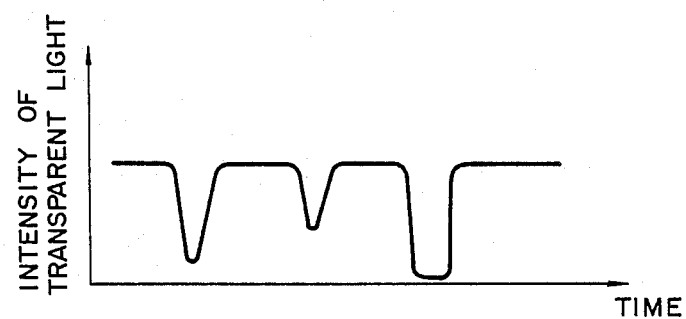
FIG. 7B is a graph illustrating dependence on time of intensity of transparent light caused by a passing particle pursuant to the FIG. 6 method.
Figure 8A:
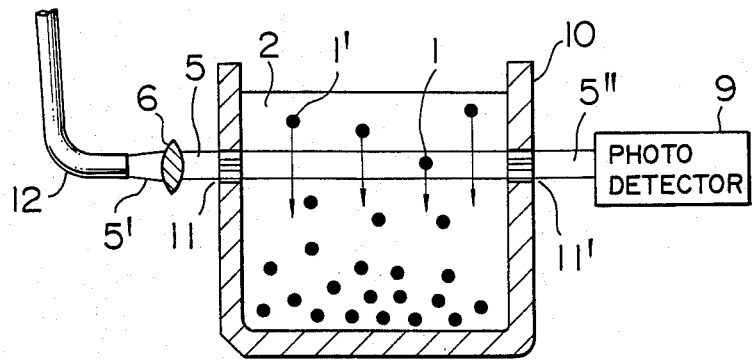
FIG. 8A diagrammatically shows the principle of another prior art inspection method.
Figure 8B:
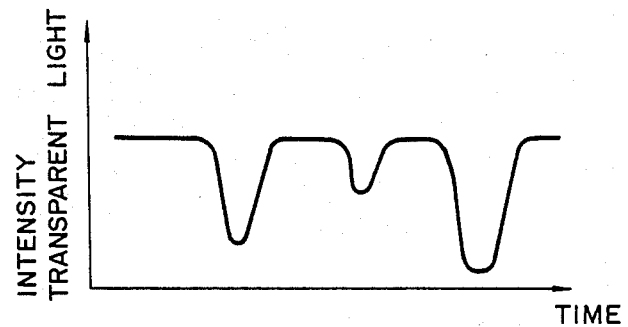
FIG. 8B is a graph illustrating dependence on time of intensity of transparent light pursuant to the FIG. 8A method.

For better understanding of the invention, the fundamental principle thereof will specifically detailed with reference to FIG. 5. In the figure, beams of light for illuminating particles travel in a direction of arrow 13, the number of the beams being indicative of a relative amount of luminous flux. The illumination light beams are thus prevailing within a solid-line parallelepiped defined by a plane ABCD and an opposing plane A'B'C'D'. The illumination light beams transfer through the parallelepiped to turn into output beams of light in a direction of arrow 14 by being decreased in their intensity when stopped by particles present in the parallelepiped. This is indicated by the illustration in FIG. 5 herein three beams of incident light designated by arrow 13 turn into two beams of output light designated by arrow 14. Assuming that particles are present between planes E'F'G'H' and E"F"G"H", beams of scattering light from the particles are radiated through a plane EFGH in a direction of arrow 15.

Naturally, the intensity of the scattering light beams increases in proportion to the number of particles prevailing within the three-dimentional region. Accordingly, by measuring the intensity of the scattering light beams travelling in the direction of arrow 15 by means of a photodetector, the number of particles present within a three-dimensional region in question can be determined, especially, the number of particles per unit volume can be determined if the volume of the region is known, on condition that the measured number is proofed or calibrated with respect to a criterion as will be described later.

The illumination light beam direction and the scattering light beam direction subtends an angle $\theta$ which is effectively 90° but may be selected so as to fall within a range of from 0° to 180°.

As is clear from the foregoing description, a first feature of the present invention resides in that beams of scattering light from a plurality of particles are counted simultaneously and in contrast to the prior art system, any sequential motion of particles is not required. For example, 100 particles can be detected simultaneously and therefore, counting can in effect be completed instantaneously by using, for example, a photodetector of 1 $\mu$s response typically standing for a conventional photomultiplier tube.

A second feature of the present invention resides in that the light illuminating and scattering light collecting units are fabricated in the form of a unitary, compact structure and therefore can be placed at a desired portion of the liquid being inspected, for example, in an upper part, a middle part or a lower part of the vessel for sedimentation, as desired. These units may otherwise be held in a recessed portion inside the vessel which is not accessible visually from the outside.

The advantageous placement of these units at a desired portion features the present invention and is attributable to the transmission of the illumination and scattering light through, for example, optical fibers. As well known in the art, the optical fibers are freely bendable to permit the transmission of light to be oriented in desired directions.

Figure 1:
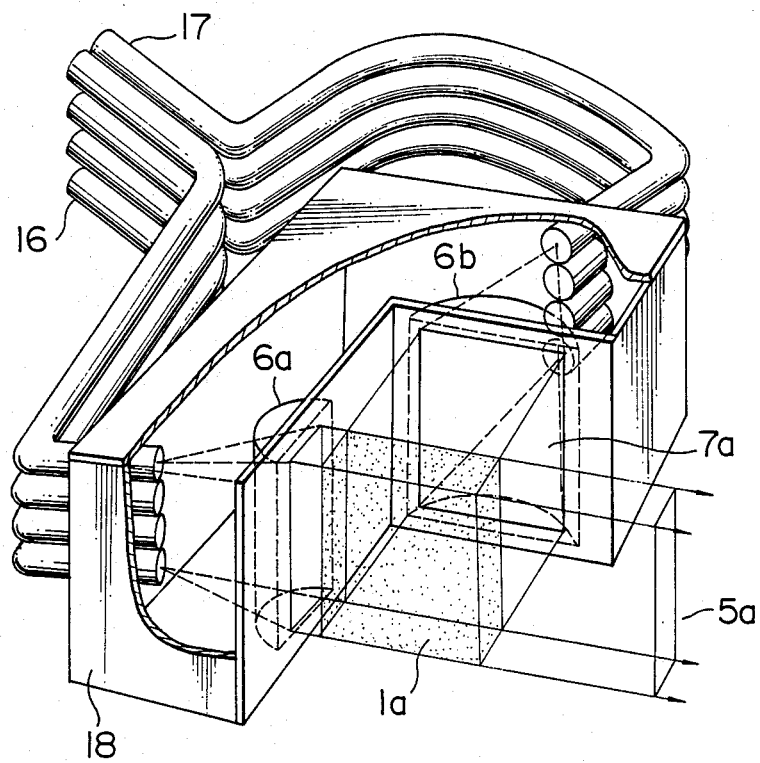
FIG. 1 is a schematic perspective view, partly exploded, of a monitor for particles of various materials according to an embodiment of the invention.
Figure 2:
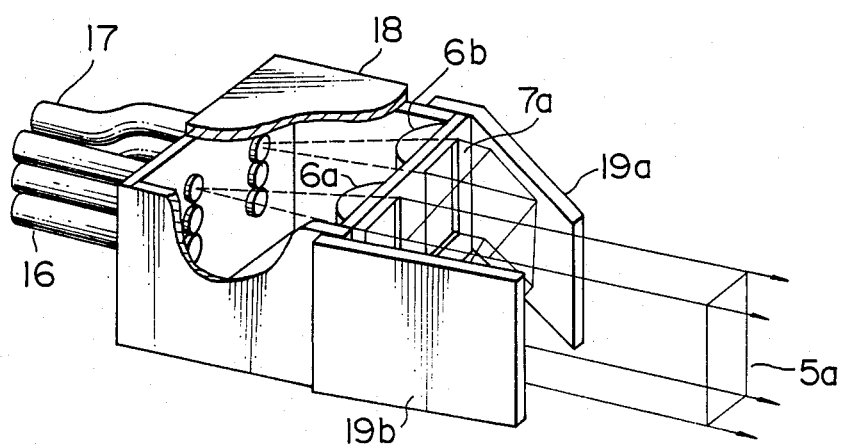
FIG. 2 is a similar view illustrating a monitor according to another embodiment of the invention.

The invention will now be described by way of example in connection with a first embodiment of a monitor for particles of various materials of the invention essential parts of which are illustrated in FIG. 1 and a second embodiment of the monitor essential parts of which are illustrated in FIG. 2.

Referring to FIG. 1, a group of particles 1a present in a liquid to be inspected are depicted as a set of dots. The particles are usually distributed throughout the liquid but the region in which particles can be detected optically is limited. Accordingly, only the group of particles 1a within a measurement region are depicted in FIG. 1 for simplicity of illustration.

A light beam 5a of a predetermined rectangular cross-sectional area illuminates the group of particles 1a. Light transmitted through a bundle of optical fibers 16 is formed by a so-called rod lens 6a into the light beam 5a. Beams of scattering light 7a from the particles 1a are collected by a rod lens 6b and captured by a bundle of optical fibers 17 through which the scattering light beams 7a are transmitted to the outside of the liquid. A box 18 is used to fix the rod lenses 6a and 6b and tips of the optical fiber bundles 16 and 17 at optically determined locations.

A unit comprised of the fiber bundles 16, 17, rod lenses 6a, 6b and box 18 can be fabricated compactly as shown in FIG. 1, measuring about 30 mm cubic and therefore, this unit (hereinafter simply referred to as a monitor head or being short therefor, head) can simply be placed in the liquid being inspected to detect a number of particles prevailing in a region at which locus of the scattering light beams 7a intersects with that of the illumination light beam 5a. In the absence of the particles, the scattering light naturally extinguishes.

In contrast to the prior art system, the particles are not counted individually in accordance with the invention. Consequently, the number of particles prevailing in a region in question can not be known directly from the intensity of the scattering light. To take care of this problem, a liquid is prepared which contains a known number of particles in unit volume and the relation between the scattering light intensity and the particle concentration is proofed using the known number of particles per volume. For monitor heads of the same configuration, the proofing is conveniently valid for one monitor head and another.

The second embodiment shown in FIG. 2 is identical, in essentiality, with the first embodiment being a FIG. 1 with the only exception of difference in sensitivity. In the embodiment of FIG. 2, the sensitivity is approximately doubled as compared to the first embodiment of FIG. 1. More specifically, as diagrammatically shown in FIG. 2, beams of scattering light generated from particles when the illumination light beam 5a transfers through the liquid are reflected, on the one hand, at a mirror 19a and, on the other hand, at a mirror 19b and reflected beams from either side are admitted to the fiber bundle 17. This second embodiment may alternatively be operable without using the mirror 19b but in such a case, part of scattering light beams oriented in the direction of the mirror 19b will be lost without being admitted to the fiber bundle 17. Advantageously, the mirror 19b prevents partial loss of the scattering light beams and reflected beams from the mirror 19b reach the mirror 19a at which they are 90° reflected toward the rod lens 6b so as to be effectively admitted to the fiber bundle 17.

In either of the two embodiments described previously, the scattering light is detected. But for the purpose of detecting particles, the transparent light may also be used. This can be easily implemented using a slightly altered head and will not be detailed herein.

To expedite understanding of the invention, the foregoing embodiments have been described by a tacit consent that the wavelength of the illumination light is equal to that of the scattering light. But the invention may obviously be applicable to detection of fluorescence. For example, where fine particles of photoresist are illuminated with illumination light of a wavelength of about 400 nm, the fine particles fluoresce at a wavelength of about 600 nm. Accordingly, by detecting the fluorescence, the photoresist fine particles can be detected.

Further, in addition to the inspection of particles in liquids, the invention may obviously be applicable to inspection of particles in solids.

Irrespective of the types of inspection differing in that either the fluorescence, the scattering light or the transparent light is used, measurement often covers the range of wavelength of visual light. Accordingly, in some applications, external light such as light for room illumination or sunlight interferes with the light for inspection. In such an event, a suitable filter may conveniently be used to eliminate the influence of the external light.

Continuous light is typically used as the illumination light but with a view of excluding the influence of, for example, sunlight which is continuous light, the illumination light may be modulated with a suitable frequency of, for example, 2KHz and the signal light such as scattering light may be detected on well-known phase difference detection basis. In this way, the effect of the external light, i.e., ambient light other than the illumination light can be minimized to greatly improve the signal to noise ratio.

Figure 3A:
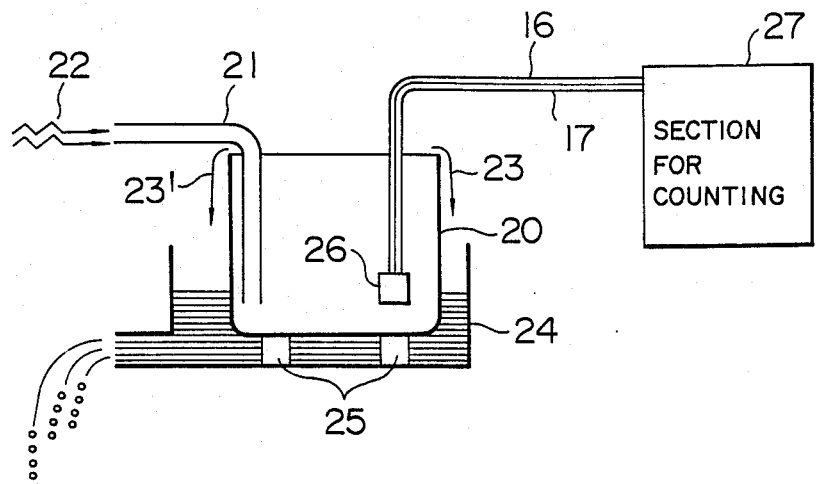
FIG. 3A is a diagram showing an example of equipment to which the monitor of the invention is applied.

FIGS. 1 and 2 illustrate the monitor heads alone, showing the essential part of the invention. Turning to FIG. 3A, there is seen an example of equipment for a practical process to which the monitor head is applied. Many processes for different purposes are involved in the semiconductor fabrication process. As a typical example, FIG. 3A shows a cleaning process using clean water. Clean water is supplied in a direction of wavy arrow 22 to a bath 20 for cleaning wafers through a pipe for water supply 21. Water overflows from the bath 20 in directions of arrows 23 and 23' and drops into a sink 24 for final drainage. The bath 20 is fixedly held on the sink 24 through supports 25. A monitor head 26 as shown in FIG. 1 or 2 is suspended from bundles of optical fibers 16 and 17 at a predetermined location within the bath 20. The optical fiber bundles 16 and 17 are directly connected to a section for counting 27 including a light source, a photodetector and units for display and recording.

Figure 3B:
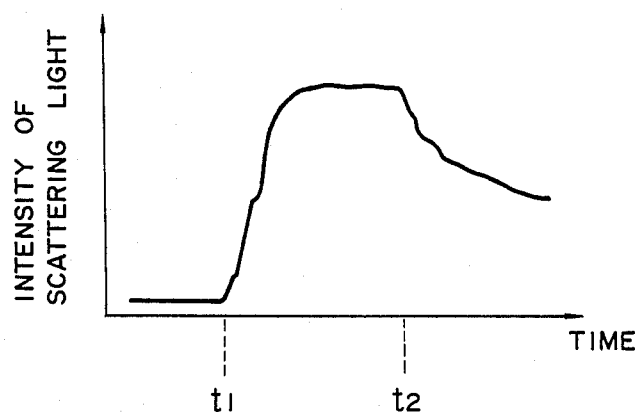
FIG. 3B is a graph showing inspection results obtained with the equipment of FIG. 3A.

A measurement result of intensity of scattering light is exemplified in FIG. 3B. When a wafer (not shown) is inserted into the bath 20 at time $t_1$, particles brought into the bath 20 along with the wafer cause the intensity of scattering light to increase. The particles once brought into the bath are discharged to the outside of the bath 20 as the supplied water overflows and consequently, the number of particles in the bath 20 begins to decrease at time $t_2$. In this manner, changes in the number of particles in the bath 20 can be counted on real-time basis by using the monitor of the present invention.

Figure 4:
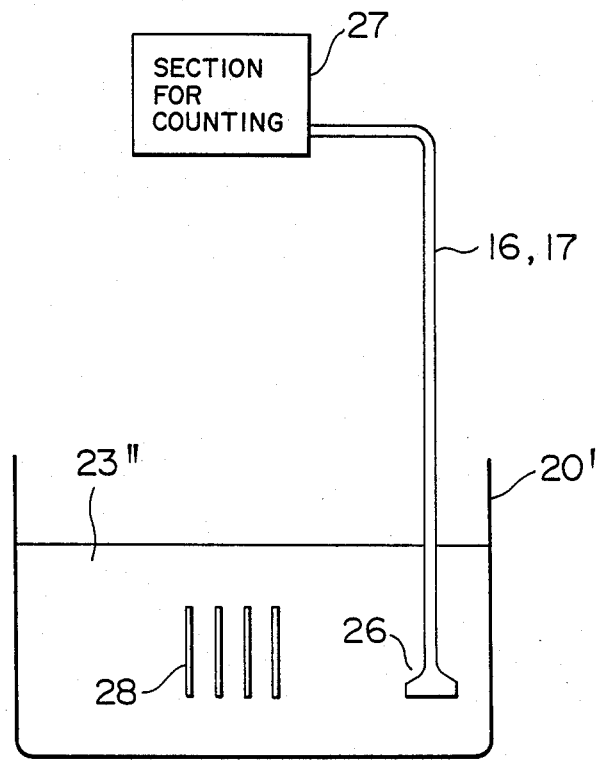
FIG. 4 is a diagram illustrating another example of equipment to which the monitor of the invention is applied.

FIG. 4 shows another example of equipment for a silicon treatment process in which particles in a hydrofluoric acid liquid have to be detected. The hydrofluoric acid liquid stands for unusual chemicals which have hardly been handled as an object to be inspected by the prior art system. This is mainly because such glass vessels as made mainly of quartz all dissolve in hydrofluoric acid and can not be used as a container for the hydrofluoric acid liquid.

Likewise, direct insertion of the lens, optical fibers and the like made mainly of quartz into the hydrofluoric acid liquid is not allowed. Considering that an optical fiber made of other materials than quartz is impractical in view of loss of light in transmission, it is practically impossible to use any optical fibers made of a material other than quartz.

Thus, in the example of FIG. 4, the lens, optical fiber bundles 16, 17 and the like are covered with fluorine contained polymer which is free from erosion by hydrofluoric acid. In particular, ends of the fiber bundles 16, 17 exposed to the liquid are fixedly put together within an area of, for example, 10 mm × 30 mm and the fluorine contained polymer is coated around the ends to a thickness of, for example, 0.1 mm.

Since the light comes in and out through the end surfaces of the fiber bundles 16, 17 and lens surfaces, it is desirable that the thickness of the fluorine contained polymer coatings on these surfaces be as small as possible. Thin coatings of fluorine contained polymer can be deposited on an object without difficulties by using techniques known in the field of, for example, pan production, proving that the fluorine contained polymer is feasible for coating on the fiber bundle end surfaces and lens surfaces to a thickness of less than several microns.

A vessel 20' made of fluorine contained polymer contains a suitable amount of hydrofluoric acid liquid 23" in which semiconductor wafers 28 are placed so that thin layers of silicon dioxide on the semiconductor wafers may be removed. In this process, the hydrofluoric acid liquid is admixed with particles taken off from the surfaces of the thin layers of silicon dioxide. Light signals detected by the head 26 for detection of, for example, scattering light are transmitted through the fiber bundle 17 to the section for counting 27 incorporating the photodetector and other units which converts the light signals into an electrical signal and displays, records and decides the magnitude of the electrical signal, light from the light source also incorporated in the counting section 27 is transmitted as illumination light into the hydrofluoric acid liquid through the fiber bundle 16.

In this manner, the real-time counting of particles in hydrofluoric acid liquid, which has hitherto been proven difficult to perform, can be accomplished. Accordingly, in an event that the number of particles in the hydrofluoric acid accidentally increases, the process can be remedied by immediately stopping operations and exchanging the soiled liquid with a fresh liquid. Since changes in concentration of particles in the liquid being inspected can be counted on real-time basis, the ending of wafer cleaning, for example, can be determined quantitatively by using a predetermined limit number of the particles. In addition, an optimum amount of clean water to be supplied can be determined from counting results, thereby permitting realization of automatic control of the water supply amount wherein, for example, the amount of water for supply can be increased automatically as the number of particles increases. It should be appreciated that the prior art system undoubtedly fails to count the particles in liquids on real-time and quick-response basis featuring the present invention.

If the concentration of particles in the liquid used for cleaning wafers is high in the vicinity of the wafers, some particles will again deposit on the wafers once cleaned. This means that the number of particles near the wafers should be counted. The present invention can meet this requirement by simply moving the monitor head to the vicinity of the wafers.

We claim:

1. A monitor for particles of various materials comprising:
    means for illuminating a liquid medium to be inspected with an illumination light beam of a predetermined cross-sectional area in a predetermined direction, said illuminating means including a bundle of optical fibers piled up vertically and having the longitudinal axes thereof extending substantially parallel to one another so as to transmit illuminating light beams therealong, and a rod lens disposed proximate to ends of the bundle of optical fibers for forming the illuminating light beams emitted from the bundle of optical fibers into said illumination light beam of the predetermined cross-sectional area in the predetermined direction;
    means for detecting a change in said illumination light beam illuminated in the predetermined direction caused by the particles contained in the inspected liquid medium in a direction substantially perpendicular to the predetermined direction, the detecting means including a rod lens for collecting beams of light from the particles in the direction substantially perpendicular to the predetermined direction of said illuminating light beam, a bundle of optical fibers piled up vertically and having the longitudinal axes thereof extending substantially parallel to one another, ends of the bundled optical fibers being disposed proximate to the rod lens for receiving the collected light therefrom, and a detector for detecting the light from the bundle of optical fibers, said illuminating means and said detecting means being of a unitary structure; and
    means for counting an amount of the particles contained in the inspected liquid medium by using a change in intensity of the changed light beam.

2. The monitor according to claim 1, wherein said illumination light beam is a light beam modulated in intensity with a predetermined frequency, and said detector includes means for phase detecting the changed light beam by using the frequency.

3. The monitor according to claim 1, wherein the changed light beam is represented by one of a scattering light beam from the particles, a fluorescence beam from the particles and a transmitted light beam which decreases in intensity when said illumination light beam is stopped by the particles.

4. The monitor according to claim 1, wherein each of said illuminating means and detecting means is covered, at its surface exposed to the liquid medium being inspected, with fluorine contained polymer.

5. The monitor according to claim 1, wherein the changed light beam is a scattering light beam from the particles.

6. The monitor according to claim 1, wherein the changed light beam is a fluorescence beam from the particles.

* * * * *